US008753381B2

(12) United States Patent
Henriksson et al.

(10) Patent No.: US 8,753,381 B2
(45) Date of Patent: Jun. 17, 2014

(54) APPARATUS AND METHODS FOR DETERMINING A PROPERTY OF A TISSUE

(75) Inventors: Par Hakan Henriksson, Lund (SE); Karl-Goran Tranberg, Lund (SE)

(73) Assignee: Clinical Laserthermia Systems AB, Lund (SE)

( * ) Notice: Subject to any disclaimer, the term of this patent is extended or adjusted under 35 U.S.C. 154(b) by 1115 days.

(21) Appl. No.: 12/680,635

(22) PCT Filed: Sep. 26, 2008

(86) PCT No.: PCT/SE2008/051089
§ 371 (c)(1),
(2), (4) Date: Mar. 29, 2010

(87) PCT Pub. No.: WO2009/041912
PCT Pub. Date: Apr. 2, 2009

(65) Prior Publication Data
US 2010/0217360 A1   Aug. 26, 2010

(30) Foreign Application Priority Data
Sep. 28, 2007   (SE) ...................................... 0702204

(51) Int. Cl.
*A61B 18/08* (2006.01)
*A61B 18/14* (2006.01)
*A61F 7/00* (2006.01)
*A61B 5/05* (2006.01)

(52) U.S. Cl.
USPC ................. 607/96; 600/547; 606/27; 606/28; 606/29; 606/30; 606/31

(58) Field of Classification Search
USPC ........................ 607/96; 600/547; 606/27–31
See application file for complete search history.

(56) References Cited

U.S. PATENT DOCUMENTS

| 5,069,223 A | * | 12/1991 | McRae | .......................... 600/547 |
| 5,843,026 A |   | 12/1998 | Edwards et al. | |

(Continued)

FOREIGN PATENT DOCUMENTS

| DE | 39 31 854 | 4/1991 |
| DE | 10 2004 041 681 A1 | 2/2006 |

(Continued)

OTHER PUBLICATIONS

European Patent Office, Supplementary European Search Report dated Aug. 4, 2011 in European Parent Application No. EP 08 83 4660, 6 pages.

(Continued)

*Primary Examiner* — Linda Dvorak
*Assistant Examiner* — Kaitlyn Smith
(74) *Attorney, Agent, or Firm* — Inskeep IP Group, Inc.

(57) ABSTRACT

An apparatus for determining a thermal property of tissue includes a base unit with one or more energy source and at least two, preferably detachable, leads. The distal end of each lead, which is introduced into the tissue to be treated, has at least two longitudinally spaced temperature measuring elements to measure surrounding tissue temperature and at least two longitudinally spaced electrode surfaces for applying current to the tissue. Each distal end is also provided with an element which uses energy emitted by the sources of energy to heat up the surrounding tissue. The base unit has computing elements, current generating elements for generating an alternating current, and conductance determining elements for determining the tissue conductance between pairs of electrode surfaces based on the alternating current applied by the current generating elements to the tissue. Methods for using the device and leads for use in the device are also described.

18 Claims, 11 Drawing Sheets

(56) References Cited

U.S. PATENT DOCUMENTS

| | | | |
|---|---|---|---|
| 5,928,159 | A | 7/1999 | Eggers et al. |
| 6,210,355 | B1 | 4/2001 | Edwards et al. |
| 6,760,616 | B2* | 7/2004 | Hoey et al. .................... 600/547 |
| 7,050,848 | B2* | 5/2006 | Hoey et al. .................... 600/547 |
| 8,090,436 | B2* | 1/2012 | Hoey et al. .................... 600/547 |
| 8,388,612 | B2* | 3/2013 | Dunning et al. ................ 606/32 |
| 2002/0072686 | A1* | 6/2002 | Hoey et al. .................... 600/547 |
| 2003/0088189 | A1 | 5/2003 | Tu et al. |
| 2003/0187430 | A1 | 10/2003 | Vorisek |
| 2004/0024398 | A1 | 2/2004 | Hovda et al. |
| 2004/0044336 | A1 | 3/2004 | Shafirstein et al. |
| 2004/0181165 | A1* | 9/2004 | Hoey et al. .................... 600/547 |
| 2005/0203503 | A1 | 9/2005 | Edwards et al. |
| 2007/0123758 | A1* | 5/2007 | Miesel et al. ................ 600/301 |
| 2007/0215163 | A1* | 9/2007 | Harrington et al. ............ 128/831 |
| 2008/0172048 | A1* | 7/2008 | Martin et al. .................... 606/10 |
| 2009/0030288 | A1* | 1/2009 | Abboud et al. ................ 600/300 |
| 2009/0076409 | A1* | 3/2009 | Wu et al. ........................ 600/547 |
| 2010/0010484 | A1* | 1/2010 | Mehta et al. .................... 606/33 |
| 2010/0049081 | A1* | 2/2010 | Hoey et al. .................... 600/547 |
| 2010/0217253 | A1* | 8/2010 | Mehta .............................. 606/33 |
| 2010/0217254 | A1* | 8/2010 | Mehta .............................. 606/33 |
| 2011/0160514 | A1* | 6/2011 | Long et al. ........................ 600/2 |
| 2011/0313312 | A1* | 12/2011 | Hoey et al. .................... 600/547 |
| 2012/0143178 | A9* | 6/2012 | Mehta .............................. 606/33 |

FOREIGN PATENT DOCUMENTS

| | | |
|---|---|---|
| EP | 1 402 838 | 3/2004 |
| WO | 00/00098 | 1/2000 |
| WO | 2005/048862 | 6/2005 |

OTHER PUBLICATIONS

Pop et al., "Changes in dielectric properties at 460 kHz of kidney and fat during heating: Importance for radio-frequency thermal therapy", Physics in Medicine and Biology, Aug. 2003, vol. 48, No. 15, specially part 1 and 3.2 pp. 2509-2525.

Chin et al., "Changes in dielectric properties of ex vivo bovine liver at 915 MHz during heating", Physics in Medicine and Biology, Jan. 2001, vol. 46, No. 1, see especially abstract and part 3.3, pp. 197-211.

Esrick et al., The effect of hyperthermia-induced tissue conductivity changes on electrical impedance temperature mapping, physics in medicine and biology, Jan. 1994, vol. 39, No. 1, pp. 133-134.

Chin et al., "Changes in the dielectric properties of rat prostate ex vivo at 915 MHz during heating", International Journal of Hyperthermia, Aug. 2004, vol. 20, No. 5, pp. 517-527.

International Search Report dated Jan. 8, 2009, from corresponding PCT application.

* cited by examiner

| Temperature °C | Conductance (mS) | |
| --- | --- | --- |
| Tumour | @ 44 kHz | @ 1 MHz |
| 32 | 3.310 | 4.747 |
| 33 | 3.348 | 4.828 |
| 34 | 3.386 | 4.909 |
| 35 | 3.424 | 4.99 |
| 36 | 3.462 | 5.071 |
| 37 | 3.500 | 5.152 |
| 38 | 3.538 | 5.233 |
| 39 | 3.576 | 5.314 |
| 40 | 3.614 | 5.395 |
| 41 | 3.652 | 5.476 |
| 42 | 3.690 | 5.557 |
| 43 | 3.728 | 5.638 |
| 44 | 3.766 | 5.719 |
| 45 | 3.812 | 5.8 |
| 46 | 3.850 | |
| $t_{coef}$ | *0.038 mS/°C* | *0.081 mS/°C* |

Fig. 6

APPARATUS AND METHODS FOR DETERMINING A PROPERTY OF A TISSUE

FIELD OF THE INVENTION

The present invention relates to devices and methods for determining a property of a tissue.

BACKGROUND OF THE INVENTION

The liver is the most common site for tumours, which may be either primary or secondary (metastases). In the Western world hepatic tumours usually represent metastatic disease. The main cause of death for patients with colorectal cancer (incidence: about new 6,000 cases in Sweden in 2004) is the presence of liver metastases, which affect about half of these patients. Breast cancer is the most common cancer in women with 6,900 new cases in Sweden in 2004. Prostate cancer is the most common cancer in men with a current incidence of 9,900 patients/year in Sweden. Lung cancer is the third most common cancer in Sweden, with 3,200 new cases each year. Cancer of the pancreas accounts for about 2% of new cancer (900 new cases in Sweden in 2004) but has a poor prognosis. The relative 10-year survival rate is 1.3% for women and 1.5% for men. It is particularly important to find a better therapy for this disease. The above-mentioned cancers are examples of solid tumours that are suitable for interstitial thermotherapy.

Therapy of Solid Tumours
Standard Treatments.

Surgical resection is the mainstay of treatment with curative intent and is combined with adjuvant chemotherapy in diseases for which cytostatic drugs have a demonstrable effect. Chemotherapy is the sole treatment when the aim of treatment is palliative. Cytostatic drugs are usually given systemically via the intravenous or oral routes but may also be given regionally via intra-arterial infusion. Irradiation seems to be inferior to surgical resection with regard to local efficacy.

Minimally Invasive Therapies, Including Local Destruction Methods.

Some methods, like radiofrequency ablation (RFA), laser-induced hyperthermia, cryotherapy and percutaneous ethanol injection (PEI) have been used rather extensively. Others like microwave coagulation or photodynamic therapy, have been used less often in patients with solid tumours. Some, like electrochemotherapy or high intensity focused ultrasound, are being developed.

As compared to surgical resection, the advantages of local tumour destruction include a) selective tissue damage which leads to a smaller immunosuppression and a smaller release of growth factors, b) minimal treatment morbidity and mortality, and c) the possibility to use chemotherapy in a more efficient way since chemotherapy can be started before or at the time of local therapy.

Interstitial Laser Hyperthermia

Interstitial laser hyperthermia is a thermal technique, which destroys tumours by absorption of light. Early experimental and clinical studies used an Nd-YAG laser and bare fibres inserted into the centre of a tumour, which created lesions that were 1.5 cm in diameter or less. It was soon apparent that clinical application would require larger lesions and improved control of the tissue effect. Methods to improve lesion size included multi-fibre systems, diffuser type fibres and vascular inflow occlusion. However the standard application of interstitial laser hyperthermia results in evaporisation and carbonisation of tissue and relatively unpredictable tissue damage and lesion size. This has led to the development of feedback control systems that monitor temperature within tissue by means of temperature sensors placed at various distances from the point of treatment and which are interfaced with a computer and a laser. The idea of these systems is that the laser output is adjusted to return the monitored temperature to the desired temperature level when the monitored temperature rises above a set temperature or falls beyond a set temperature. It is thus possible to maintain a substantially constant temperature over a desired period of time at the measuring points which surround a known volume of tissue, which is intended to give a high degree of precision with respect to both lesion size and type of cellular damage.

One of the advantages of feedback control of the treatment effect is that it ensures reproducible and cytotoxic temperatures in the periphery of tumour tissue. Another way to control lesion size is to use a dose planning system, which enables lesion size to be calculated for different tissues, output powers and treatment durations. Planning of local treatment can also be integrated with computer aided image analysis to give information about the size and location of tumours, vessels and bile ducts in 3-D views.

However such methods only determine the temperature in the vicinity of the temperature sensor(s) and give no information on whether the required temperature has been achieved throughout the tissue that is supposed to be treated.

Interstitial Laser Thermotherapy (ILT)

Interstitial laser thermotherapy (ILT) is a variant of interstitial laser hyperthermia where the focus is on killing tumour cells at temperatures of 46-48° C., i.e. at temperatures that do not cause tumour antigens to coagulate. Consequently ILT eventually produces cell death while still allowing the presentation of intact tumour antigens. These cause an inflammatory local reaction and this can produce an efficient immune response, both in rats and in human patients. This is in contrast to ablative techniques that use higher temperatures and thus cause instantaneous necrotisation of the tissue. This is also in contrast to traditional hyperthermia that uses significantly lower temperatures, i.e. <42.5° C., and long exposure times.

For feedback control of the laser power one or more thermometers (thermistors or thermocouples) placed within the tumour and/or at the tumour boundary have commonly been used. One of the disadvantages with this type of monitoring is that it requires interstitial positioning of probes and thus additional preparations. It is advantageous to encase the monitoring device, e.g., a thermistor probe, with the laser fibre close to the laser tip, avoiding separate punctures for temperature measurement.

A problem that has occurred during feedback control using thermometers is that they only measure the local temperature and are unable to detect if overheating (or insufficient heating) occurs in tissue which is not close to the thermometer. Overheating is undesirable as it may lead to carbonisation and/or necrotic breakdown of the tissue. Carbonisation may be present as a black layer surrounding the heat source which layer impairs light penetration and reduces the distance that light can propagate in the tissue. Rapid necrotic breakdown can cause poisoning. Insufficient heating is undesirable as it leads to ineffective treatment of the tissue. Attempts to determine changes in the electrical properties of tissue caused by heating have used implanted leads provided with electrodes to measure the impedance or transfer properties of the tissue and thermistors or thermocouples to measure temperature—tissue impedance thermography. Using different frequencies for the current used in impedance measurements it is possible to measure impedances in tissue local to the measuring electrodes as well as tissue further away. However the results have hitherto been considered unreliable as the values of the impedance or transfer property obtained when the temperature readings reach an elevated steady state (i.e. a constant temperature, for example 46° C.) have changed continuously in such a way that it appears that they are drifting—see FIG. 4 and FIG. 5. These figures show temperature and impedance against time at three distances from the laser tip. Both graphs have a similar pattern showing that changes in the measured tissue properties, in this case the measured impedance, follow changes in the tissue temperature, and that an irreversible change in the impedance occurs such that the impedance at, for example, 40° C. at the beginning of the experiment is not the same as the impedance at 40° C. at the end of the heating phase. Similarly FIG. 6, which shows conductance against temperature for a tumour using information gathered from the experimental results shown in FIG. 2 "Conductance versus temperature at 44 kHz and 1 MHz for an EMT6 tumour in vivo" in "The effect of hyperthermia-induced conductivity changes on electrical impedance temperature mapping", M A Esrick, D A McRae, Phys. Med Biol. 39 (1994) 133-144, shows that the conductance of EMT6 tumour tissue in vivo while being heated from 37° C. to 45/46° C. over a period of 19 minutes varies substantially linearly. From this figure it is possible to determine that the conductivity of this tissue at a current frequency of 44 kHz and 37° C. is around 3.5 mS, at 46° C. it is around 3.85 mS. Looking at this limited range the thermal coefficient is 0.038 mS/° C. when measured at 44 kHz. When measured at 1 MHz the conductivity at 37° C. is around 5.152 mS, at 45° C. it is around 5.8 mS. Looking at this limited range the thermal coefficient is 0.081 mS/° C. when measured at 1 MHz.

Cancer Therapy Using Laser Devices

Mueller et al (DE 3931854, 1991) presented an invention based on an MRI tomograph for tumour location and monitoring during interstitial laser irradiation of tumours, e.g., in the liver, via quartz light conducting fibres. The invention was said to relieve the patient from surgery, long hospitalisation and to enable tumour removal with small side effects for the patient. In this invention a multiplanar x-ray device is coupled to the MRI tomograph to enable the fibres to be placed in the tumour using point ion probes and the coordinates of the tumour to be determined by MRI tomography.

When performing an interstitial heat treatment of cancer tumours a feedback system that is able to present information to the user regarding the progress and outcome of the treatment is crucial. In prior art devices and methods, treatment is often performed based on experience collected during previous treatments and the session time is set based on this knowledge. As a secondary means for treatment control, the tissue temperature may be monitored at a limited number of measurement points. In many cases the treatment time is set to a period longer than that which is actually required as reliable means for feedback regarding how the tissue is responding to the heating, the "tissue effects", do not exist. For the same reason the desired result can not be obtained in many cases as the temperature distribution is not uniform in the target area and proper positioning of the temperature sensors can not be ensured. As a temperature sensor can only sense the local temperature there is no way of checking if there are cold spots outside the local area, such cold spots being caused, for example, by blood vessels passing through the tissue and conducting away the heat.

SUMMARY OF THE INVENTION

Using the present invention it is possible to overcome at least some of the problems with prior art devices and methods for thermal treatment of tissue. In a first aspect of devices and methods in accordance with the present invention a tissue electrical property which varies with temperature is monitored across a portion of the tissue being treated while a feedback system controls the heating of the tissue to maintain a desired elevated tissue temperature, and the treatment is determined to be complete when, at the maintained desired tissue temperature, substantially no further changes are detected in the monitored electrical property.

In a second aspect of devices and methods in accordance with the present invention, by initially establishing data regarding the tissue properties and then combining this data with the temperature measurements in known positions with regard to the heat source and further combining this information with two- and/or three-dimensional electrical property measuring (i.e. tissue transfer function and/or conductivity and/or impedance measurement) and correlating the actual changes of these properties in the tissue to the expected change in tissue properties based on the initial data, it is possible to extract information in a three-dimensional space regarding the non-reversible tissue effect that is a result of ongoing heat treatment. It is subsequently possible to determine the point in the treatment where the desired tissue effect has been obtained and to inform the user that the treatment is complete and successful. Furthermore it is also possible to detect when ongoing treatment is failing to achieve the expected change in tissue properties and to provide a signal to an operator that the treatment is not proceeding as planned.

The present invention achieves this by providing implantable leads, each provided with impedance measuring electrode surfaces and temperature measuring means, the leads being connectable to a base unit provided with current generating means, measuring means for measuring the electrical property of the electrical path between 2 electrode surfaces and control means, the control means being adapted to use electrical property and temperature readings from the leads to determine a temperature-dependent property of tissue in which the leads are implanted.

BRIEF DESCRIPTION OF THE FIGURES

FIG. 6 shows experimental data which indicates that changes in tissue conductance are linear following slow heating to 46° C.;

DETAILED DESCRIPTION OF THE INVENTION

In the following, directions are given in respect to the skin of a patient or the surface of an organ or tissue, thus the expression "above" means outside the skin or outside the surface of an organ or boundary of a tissue and is not dependent on the actual orientation of the patient, organ or tissue. Depths or levels or distances inside or outside a patient or organ are, unless otherwise stated, measured in the direction perpendicular to the skin of the patient or the surface of an organ or tissue. Distances between components are measured from edge-to-edge unless otherwise stated.

Figure 1:
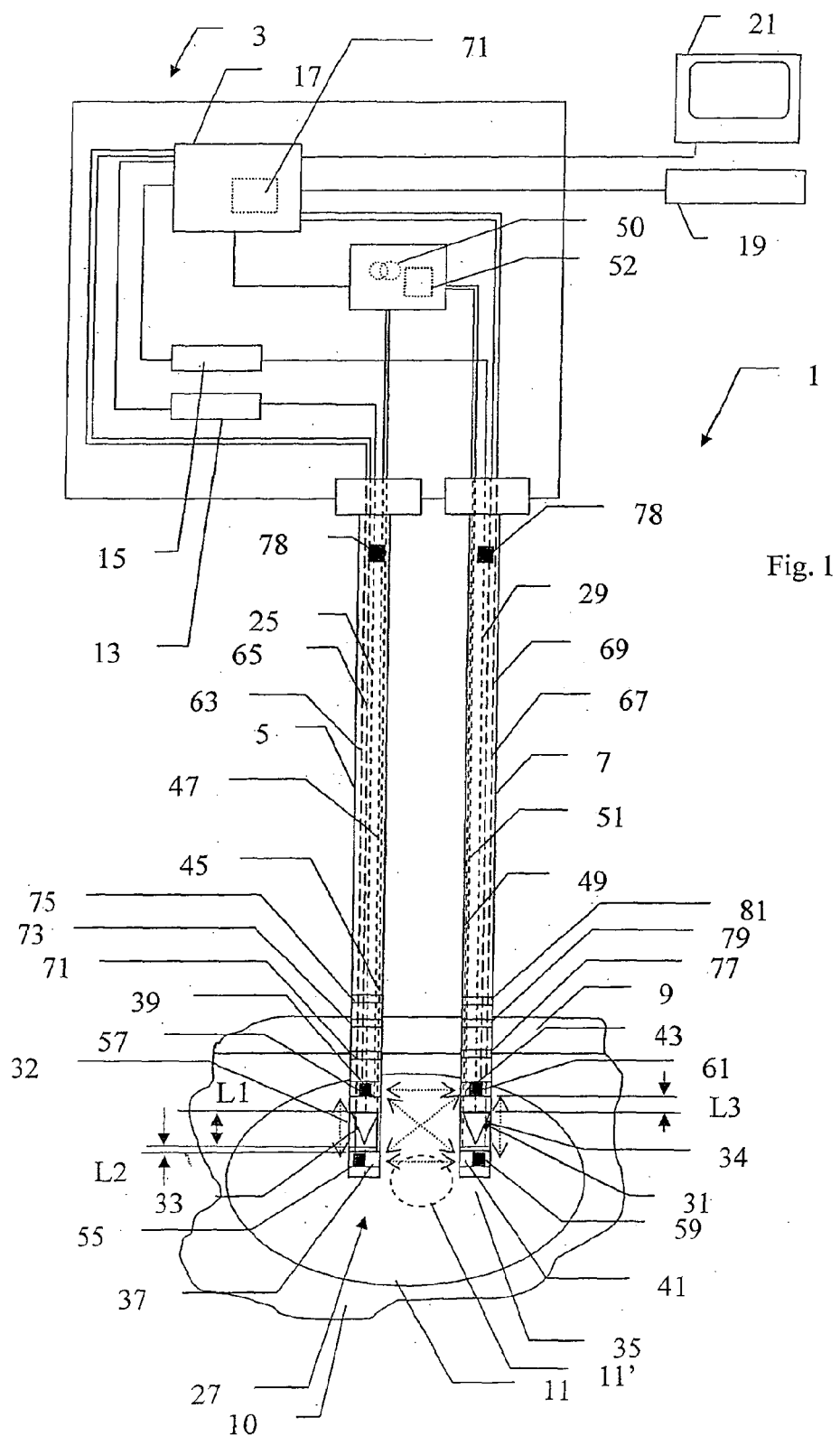
FIG. 1 shows schematically a first embodiment of a thermal device in accordance with the present invention.

A first embodiment of a thermal device in accordance with the present invention is shown schematically in FIG. 1. Thermal device 1 comprises a base unit 3 and a plurality of insertable leads. In this example, in order to avoid clutter in the illustration, the thermal device 1 has been represented as having just two leads 5, 7 but in practice it is possible that only one lead will be used for example for the treatment of small tissue volumes and that more than 2 leads will be used for example for the treatment of larger volumes of tissue. Larger number of leads can be used if it is desired to reduce treatment time, or if they are required for reasons of efficiency for example if the maximum extension of the tissue being treated is larger than can be reliably treated with just two leads— typically when using lasers as the source of energy, leads are placed 2-3 cm apart. Preferably each lead 5, 7 is easily detachable from base unit 3 so that leads can be easily replaced for reasons of hygiene when a different patient is to be treated. The distal end of the each lead 5, 7 is intended to introduced though the skin 9 of a patient into, or into the vicinity of, the tissue to be treated e.g. tumour tissue 11. Preferably, to enable accurate positioning, at least the portion of each lead intended to be inserted into a patient is made sufficiently rigid so that it doesn't bend during insertion and use.

Base unit 3 may comprise one source of energy attached to a plurality of leads, but preferably it comprises a plurality of sources of energy. In this embodiment one source of energy in the form of an infrared laser 13, 15 is provided for each lead 5, 7, so in this example base unit 3 comprises 2 lasers, the output of each laser 13, 15 being controllable individually. Preferably each of said laser 13, 15 has a maximum optical output power level in the region of 1-50 watts. The lasers preferably provide light energy of a wavelength that is efficiently absorbed by animal tissue in order to heat said tissue. Preferably the lasers operate in the wavelength range of 700 to 1300 nm, more preferably at 805 or 1064 nm. Preferably each source is a solid-state semiconductor laser as these have small dimensions and high efficacy. Alternatively each source of energy could be an Nd-YAG laser or similar, however these devices have the disadvantage of being less efficient and larger than semiconductor lasers. Preferably the optical output power of each laser can be independently controlled by a control system such as a microprocessor or microcomputer 17, arranged in base unit 3, and provided with appropriate operating software and hardware. Preferably base unit 3 is provided with user input means such as at least one keyboard 19, mouse, touch screen, tablet or the like, to enable a user to control the operation of the system and display means 21 such a screen, monitor, light panel, or other display to provide measured and/or calculated and/or processed information to the user. Such information can include for example, one or more of the electrical properties of the tissue between electrodes, the position of leads with respect to each other and/or the target tissue to be treated, and tissue temperatures.

The output laser light from laser 13 can be fed to an optical fibre 25 which is inside lead 5 and extends to the distal end 27 of lead 5. The output laser light from laser 15 can be fed to an optical fibre 29 which is inside lead 7 and extends to the distal end 35 of lead 7. Each distal end 27, 35 is provided with a tissue heating element, in this example a laser light transparent energy emission window 32 resp 34 or bare fibre tip at a short distance, e.g. between 0 and 40 mm, from the extremity of the distal end 27, 35. Preferably each window has a length L1 of between 1 and 15 mm. In this embodiment an optical fibre tip 31, resp. 33 through which laser light is transported to the distal end 27, 35 is positioned in each window so that the laser light can leave the lead 5, 7, be absorbed by, and heat the surrounding tissue. The optical fibre tip can be in the form of a bare fibre, a diffuser or some other means to guide the distribution of the laser light.

Each distal end 27, 35 is further provided with spaced apart distal and intermediate electrode surfaces, for example in the form of conducting electrode plates, wires, projection, depressions or, as shown here, electrode rings 37, 39, resp. 41, 43. Electrode surfaces are made from conductive media such as silver, platinum, gold or similar and during a treatment it is intended that said electrode rings are in electrical contact with the tissue. Preferably the width of an electrode surface in the longitudinal direction of a lead can be from 0.1 mm to 5 mm, preferably 0.5 to 2 mm, although larger or smaller dimensions are also conceivable. Optionally a conductive paste, gel, liquid or similar may be provided to the electrode surfaces during use to ensure reliable electrical contact. Distal electrode rings 37, 41 may be placed closer to the extremity of each lead 5, 7 than said windows 32, 34 and are preferably within a distance L2 of 0-10 mm from the distal end of windows 32, resp 34. Intermediate electrode rings 39, 43 are positioned further away from the extremity of their respective leads preferably at a distance of L3 of 0-40 mm from the proximal end of window 32, 34. Thus in this embodiment of the present invention each window 32 resp. 34 may be positioned between a pair of electrode rings 37, 39 resp. 41, 43.

Note that if, as disclosed above, window 32, 34 is placed at the extremity of the lead, (i.e. 0 mm from the extremity) then the pair of electrode surfaces (and any further electrode surfaces) are positioned further away from the extremity than the window and are longitudinally spaced apart. Preferably the longitudinal distance between a pair of neighbouring electrode rings on a lead is less than 55 mm, more preferably less than 40 mm, e.g. 6 mm or 10 mm, and preferably is greater than 3 mm.

Electrode rings 37, 41 are longitudinally separated from electrode rings 39, 43 by a distance L1+L2+L3. While L1, L2 and L3 for lead 5 may be same as L1, L2 and L3 for lead 7 and, in the event additional leads are used, all additional leads it is not a necessity but to permit accurate positioning it is necessary that the distance between electrode surfaces on each lead is known.

Figure 3:
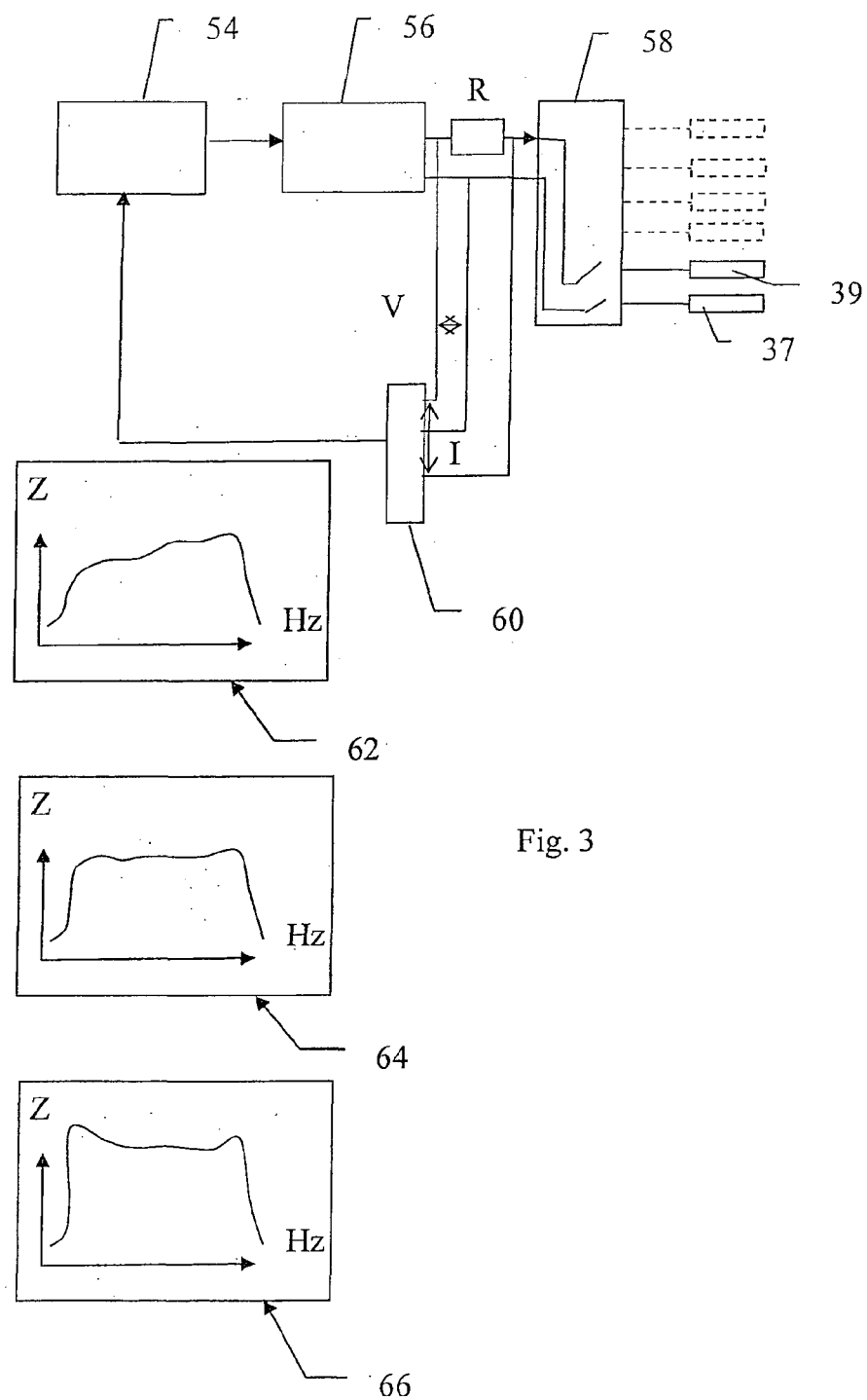
FIG. 3 shows schematically a first embodiment of a digital system for measuring the electrical properties of tissue.
Figure 4:
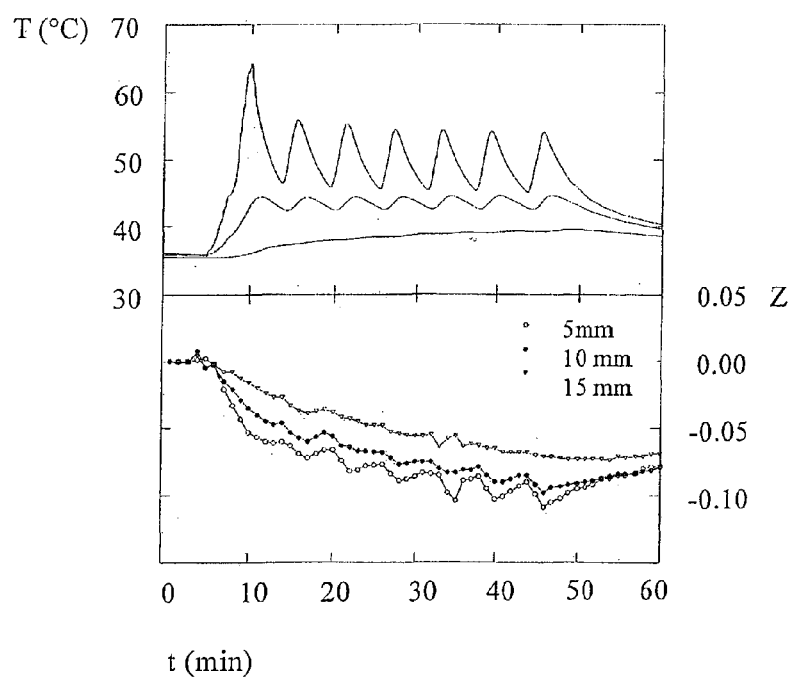
FIGS. 4 and 5 show experimental results of impedance and temperature against time during heating and cooling of tissue.
Figure 5:
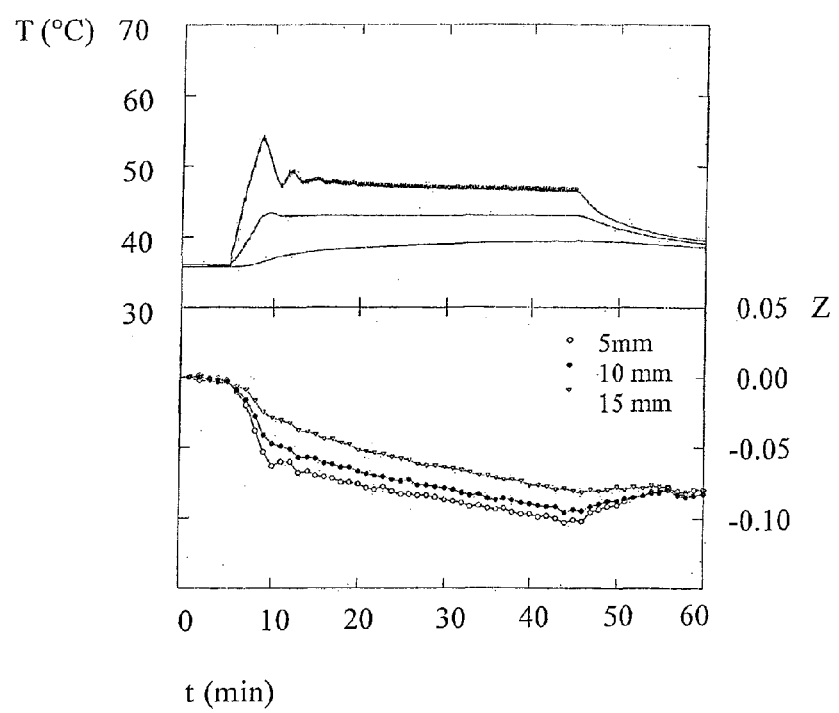

Each electrode ring 37-43 is connected by its respective electrical conductor 45, 47, 49, 51 to the switchable output of a current generator 50 and the switchable inputs of a measuring circuit 52 preferably able to measure an electrical property of the electrical path between any pair of electrode rings. In order to illustrate the present invention an embodiment is now described in which circuit 52 is a conductance measuring circuit of the type well-known in the prior art which comprises an amplifier and analogue-to-digital converter. The use of other measuring circuits which measure one or more of the properties conductance, resistance, impedance and capacitance is also conceivable. Current generator 50 is controllable to produce alternating current of known amplitude and, preferably, known phase and, preferably, is switchable between at least two frequencies, one low frequency, for example less than 500 Hz or 1 kHz or 5 kHz or 10 kHz or 50 kHz or 100 KHz and one high frequency e.g. greater than 200 kHz or 500 kHz or 1 MHz or 2 MHz. The possibility of using different frequencies during conductance measuring allows the conductance of different volumes of tissue to be measured (and the conductivity to be calculated if the conduction path length is known)—a form of tomography. This is because the current path between electrodes depends partly on the frequency used—lower frequency currents, e.g. 1 kHz, follow curved paths between electrodes while higher frequencies, e.g. 100 kHz, follow more direct paths. Current generator 50 and conductance measuring circuit 52 are controllable by control system 17 so that, preferably, it is possible to measure the conductance between any pair of electrode rings 37-43, 71-81 and at any desired frequency. This can be achieved, for example by using digital storage means and a digital to analogue converter 56. An example of such a digital system for measuring the electrical properties of tissue, shown schematically in FIG. 3, could comprise digital storage means in the form of digital memory 54 containing a signal loop which produces a cyclical signal which sweeps from a low frequency (e.g. 500 Hz) to a high frequency (e.g. 200 kHz) over a period of a few seconds, e.g. 5 seconds or 10 seconds and then repeats. This signal is transmitted to a digital to analogue converter 56 connectable by a multiplexer 58 to any pair of electrode rings—which electrode rings could be on the same lead or on different leads. The resulting electrical properties of the tissue between this pair of electrode rings are then sampled and converted to a digital signal by signal conditioner 60 and the values of the properties recorded in the memory 54 against the signal which caused them. As shown in FIG. 3, these recorded signals can be used to produce a representation 62, 64, 66 of the transfer function in the frequency domain of the tissue that the electrodes are in. Each type of tissue has a certain transfer function depending on density, cell size, vascularity, etc. The electrical properties e.g. the conductance or impedance or transfer function of the tissue will change during thermal treatment as the physical properties of the tissue change and thus the transfer function in the frequency domain of the tissue will change as the tissue changes. Reference 62 shows a hypothetical representation in the frequency domain of tissue in a first state, e.g. before thermal treatment and reference 64 shows a hypothetical representation of the same tissue during a step in thermal treatment of the tissue where the temperature of the tissue is higher than that of the tissue in the first state. Reference 66 shows a hypothetical representation in the frequency domain of the same tissue after it has been killed by thermal treatment.

An improved digital system for measuring the electrical properties of tissue could have two signal channels. The first channel having a signal loop of the type mentioned above and the second channel containing a synchronisation signal which is used to synchronise the measurement and to improve the resolution in time. The synchronisation signal can be organised as one synchronisation pulse per sweep (in combination with a controller system that ensures that the following samples are timed correctly) or one pulse for each sampling point. The solution is very simple and in spite of this it will enable very complex measurements. A digitalised sweep signal, for instance from 500 Hz or 1 kHz to 100 kHz or 2 MHz or white noise or pink noise or the like having a certain pattern is stored in the digital memory device. The digital data is fed to a two channel digital to analogue converter in which channel 1 holds the sweep signal and channel 2 contains a synchronisation signal. The sweep signal is feed to an amplifier, for instance a variable gain amplifier which may be controlled from the control system in order to adjust the amplitude to the desired level. The amplifier signal is fed to a multiplexing device that allows the signal to be feed to any of the selected electrode pairs. An amplifier circuit measures the applied voltage and resulting current and phase. A resistor is connected in series with the signal path to allow current measurement. An analogue-to-digital converter and timing circuit samples the signal at times synchronised by means of the synchronisation signal with the sweep pattern fed to the electrodes. Digitised signals are stored in memory along with synchronisation information. The stored information can be fed to the control system which preferably is adapted to performing signal processing, for example an averaging of the repeated signals, that will improve the signal quality.

In the following the symbol 'Z' is used to refer to the measured electrical properties of tissue through which electricity is conducted between two sensing electrode. If measurements are taken at just one frequency then Z could be the conductance or impedance of the tissue. If measurements are taken at more than one frequency then Z would be a transfer function of the tissue It is possible to determine a transfer function in a number of ways, for example by using a number for frequencies (as described above), scanning, white or pink noise or the like in combination with FFT or FT ((Fast) Fourier Transformation)). In the following description, the device and methods of using it will be illustrated by examples where the conductance of tissue is measured but it is understood that the invention is also applicable to devices and methods where impedance and/or a transfer function of tissue is measured.

Normally the conductance of tissue increases with heating and this increase is substantially fully reversible upon cooling back to 37° C. if the tissue is only heated to approximately 5-6° C. above its normal temperature (where 37° C. is the normal temperature for human tissue). Further heating, for example to 9° C. above the normal temperature, will cause cell death (without causing cells to burst) which causes some irreversible changes in conductance along with some reversible changes in conductance—i.e. the conductance of the dead tissue when cooled back to 37° C. is not the same as its conductance at 37° C. before it was heated.

At least each distal and intermediate electrode ring 37-43 is preferably provided with its own thermal sensor such as a thermistor 55, 57, 59, 61, so that the temperature in the vicinity of the electrode ring can be measured. It is also conceivable to provide other electrode rings with their own thermal sensors. By attaching the thermal sensor to an electrode surface or building it into the electrode surface the local temperature at which conductance measurements are being made can be reliably determined. As an alternative a thermal sensor can be provided adjacent to an electrode surface.

Each thermistor 55-61 is connected by its respective pair of electrical conductors 63, 65, 67, 69 to a control circuit 71 of control system 17 which permits control system 17 to determine the temperature of each thermistor 55-61. Control circuit 71 can, for example, comprise a conventional Wheatstone bridge circuit of the type well-known to be useful for measuring temperature when used in connection with thermistors.

A plurality of depth sensing electrode surfaces for example in the form of conducting electrode plates, wires, projections, depressions or, as shown here, such as electrode rings 71, 73, 75 resp. 77, 79, 81 are placed on each lead 5, 7. Electrode rings are made from conductive media such as silver, platinum, gold or similar. Preferably the width of an electrode ring in the longitudinal direction of a lead can be from 0.1 mm to 5 mm, preferably 0.5 to 2 mm, although larger or smaller dimensions are also conceivable. Optionally a conductive paste, gel, liquid or similar may be provided to the electrode surfaces during use to ensure reliable electrical contact. First depth sensing rings 71, 77 are positioned at a predetermined distance from the respective intermediate electrode rings 39, 43, e.g. at a distance of between 5-15 mm, e.g. 5 mm or 10 mm or 15 mm, from intermediate electrode rings 39, 43 in the direction towards the proximal end of the lead. Second depth sensing rings 73, 79 are positioned a further distance away from the distal end, e.g. at a distance of between 5-15 mm e.g. 5 mm or 10 mm or 15 mm, from first depth sensing electrode rings 71, 77. Similarly third depth sensing electrode rings 75, 81 and any further depth sensing electrode rings (not shown) are positioned further away from the distal ends and preferably with the same separation of between 5-15 mm e.g. 5 mm or 10 mm or 15 mm, from the adjacent depth sensing electrode ring. It is not required that the distance between rings is the same but the distance between the rings on each lead has to be known or standardised in order to allow accurate positioning by triangulation. The actual distance between depth sensing electrode surfaces can be selected depending on the accuracy of depth measurement required. The closer together that the surfaces are, then the more accurate the depth measurements will be.

One or more leads may optionally be provided with readable memory 78 and the information regarding electrode surface positions on the lead can be stored in the memory of the lead. Preferably this information is inputted into the memory by the manufacturer of the lead. During use of such a lead the control unit can extract the information regarding electrode positions from the lead and use it in triangulation calculations. Preferably the memory is resistant to X-ray and gamma radiation in order to permit sterilisation of the leads. Preferably the memory is ferro-magnetic random access memory (FRAM). In the event that leads without memory containing information on electrode positions are used or the memory is not accessible by the control unit, preferably means are provided for user input of such information to the control unit.

Each depth sensing electrode ring 75, 81 is connected by a conductor (not shown for clarity of illustration) to the switchable output of current generator 50 and the switchable inputs of conductance measuring circuit 52. Preferably conductance measuring circuit 52 is arranged to be able to measure the conductance between any pair of distal, intermediate or depth sensing electrode rings at any desired frequency, e.g. frequencies between 500 Hz and 2 MHz.

Thermal device 1 is intended to thermally treat tissue, especially diseased tissues, for example a tumour. In order to do this, the lead or leads which will be used to heat tissue have to be accurately placed both with respect to the unhealthy tissue e.g. the cells of a tumour which has to be killed and, in the case two or more leads are used, also with respect to each other. In a first illustration of a method for positioning leads, it is intended that at least the window 32, 34, and distal electrode ring and intermediate electrode ring 37, 39, 41, 43 (and their respective thermal sensors 55, 57, 59, 61) of each of two leads is to be placed inside a tumour 11. In some cases the leads are intended to be positioned such that the window 32, 34, and distal electrode ring and intermediate electrode ring of each lead are outside the tumour—this is illustrated in FIG. 1 by a tumour 11' shown in dashed lines. The position of the tumour in relation to other features of the patients body is assumed to be known, e.g. from previously or simultaneously performed imaging. One or more leads 5, 7 are positioned on the skin of the patient immediately above the tumour and pushed thorough the skin 9 and healthy 10 tissue of the patient towards the tumour. As the exact position and/or size of the tumour may have changed since the imaging was performed and it may be difficult or impossible to determine the boundaries of the tumour with imaging methods, it is useful to determine when the windows 32, 34, and if the extent of the tumour allows, the distal ends 27, 35 and distal and intermediate electrode rings 37, 39, 41, 43 are inside the tumour 11. The relative positioning of the electrodes rings (and hence the leads they are attached to) can be determined by measuring the conductance between pairs of electrode rings. Normally the conductivity and transfer function of tumour tissue is different from healthy tissue. During insertion of a lead e.g. lead 5, the conductance between distal and intermediate electrode rings 35 and 37 is monitored. Lead 5 is positioned above the tumour 11 and is inserted through the skin towards the tumour 11. Distal electrode ring 37 enters the body of the patient first and it is then followed by intermediate electrode ring 39. No current will flow between distal electrode ring 37 and intermediate electrode ring 39 until intermediate electrode ring 39 comes into contact with tissue, at which point a certain conductance value will be measured between electrode rings 37 and 39. Next the conductance between intermediate electrode ring and first depth sensing electrode ring 71 can be monitored. No current will flow between them until first depth sensing electrode ring 71 comes into contact with the skin of the patient. As the lead is introduced further into the patient, second, third and any further depth sensing electrode rings will come into contact with the patient's tissue and the depth of the lead in the patient can be determined from knowledge of which electrode ring pairs have a conductance which indicates that they have entered the patient. Thus if the lead is intended to be inserted so that the distal end is intended to be 40 mm below the skin of the patient, and there is a depth sensing electrode ring positioned 30 mm from the distal end and a further depth measuring electrode positioned 40 mm from the distal end, then, assuming that the lead has been inserted perpendicularly to the skin of the patent, the depth of the distal end will be 40 mm below the skin of the patient when the further depth measuring electrode positioned 40 mm from the distal end comes into contact with the skin and current, preferably alternating current, starts to flow between the depth sensing electrode ring positioned 30 mm from the distal end and the further depth measuring electrode positioned 40 mm from the distal end.

During insertion of the lead, the conductance between some or all of the permutations of combinations of pairs of electrode rings can be monitored. This can be used to see if the electrical properties of the tissues through which the lead is passing are the same. Normally healthy tissue has a different conductivity to that of tumour tissue. In those cases, by monitoring changes in the conductance as a lead is being inserted into tissue, it is possible to determine changes in conductivity and hence detect when the lead has entered, or is close to, tumour tissue. For example, during insertion of the lead the conductance measured between the distal electrode ring and intermediate electrode ring is monitored or sampled after both electrode rings have entered healthy tissue. The conductance remains substantially the same until distal electrode 37 enters the tumour, or is in the immediate vicinity of the tumour, at which point the conductivity may change. If it does change, then it will continue to change until the intermediate electrode ring 39 closely approaches or enters the tumour (assuming that the tumour is deep enough to contain both distal and intermediate electrode rings). As long as both distal and intermediate electrode rings 37, 39 remain in the area of the tumour further movement of the lead should not result in any significant change in conductance between electrode rings 37 and 39. If the conductance does change unexpectedly then this could be a sign that there is a problem, for example that the distal electrode ring has exited the tumour field, or entered a blood vessel inside the tumour or there is a malfunction, and appropriate action, such as repositioning a lead or replacing a lead, would need to be taken.

Once lead 5 is at the required depth inside the tumour and if more than 1 lead is to be used in the treatment then the same procedure can be followed with lead 7 and any other leads. Preferably during insertion of lead 7 (top aid in positioning the lead) and/or once lead 7 has entered the tumour (to determine its position with respect to other leads) the distance between electrode rings on the implanted leads can be measured by triangulation—that is by measuring the conductance or transfer function between pairs of electrode rings on different leads and using this to calculate the distance between each such electrode pair. The readings between pairs of electrode surfaces can be processed in order to determine the position of the leads both with respect to the tumour (assuming its position is known) and with respect to any other leads. As the distance L2 between the electrode rings 37, 39 and 41, 43 is known, it is possible to determine the electrical properties of the tumour tissue, preferably by measuring its conductance at least two frequencies to determine its transfer function. The distance between electrode ring 37 on lead 5 and electrode ring 41 on lead 7 can be determined by measuring the conductance and/or transfer function Z (37-41) between this pair of rings. The distance between electrode ring 39 on lead 5 and electrode ring 43 on lead 7 can be determined by measuring the conductance and/or transfer function Z (39-43) between this pair of rings. If Z (37-41) and Z (39-43) are the same then electrode ring 37 and electrode ring 41 are the same distance apart from each other as electrode ring 39 is from electrode ring 43. This distance can be calculated by dividing the values of these electrical properties (conductance and/or transfer function) by the electrical properties determined previously for the known distance between the distal and intermediate electrodes on the same lead. In order to determine if the distal ends 27, 335 of leads 5 and 7 are at the same depth in the patient the conductivities and/or transfer functions between diagonally opposed pairs of electrode rings can be measured, i.e. the conductivities and/or transfer functions Z (37-43) and Z (39-41). If these are the same then the diagonal distance between electrode rings 37 and 43 is the same as the diagonal distance between electrode rings 39 and 41. If the measurements show that Z (37-41) and Z (39-43) are the same and also that Z (37-43) and Z (39-41) are the same then it can be assumed that leads 5 and 7 are parallel and have their distal ends at the same depth. If (37-41) and Z (39-43) are not the same and/or Z (37-43) and Z (39-41) are not the same then it is possible to calculate the relative position of the leads with respective to each other, i.e. how far apart they are, whether they are inclined with respect to each other and if so, at which angle(s). Preferably such calculations are made at regular intervals during insertion of the leads. Said intervals are preferably less than 10 seconds, more preferably less than 2 seconds and most preferably are less than 1 second, thereby allowing real time monitoring of the position of electrodes so that the operator implanting the leads can be given accurate and timely information regarding the position of the leads as they are being implanted. Of course it is not always intended that leads should be parallel or at the same depth, as their intended positions are dictated by the, probably irregular, shape of the tumour being treated. Using the principal of triangulation as described above it is possible to verify if leads have the intended positioning with respect to each other and, preferably, the tumour.

It is conceivable that the collected signals and the resulting data including, but not limited to, calculated distances and angles between leads, signal phase, voltage and/or current amplitudes, tissue properties such as impedance, conductance and tissue effect temperature could be presented to an operator through an operator interface. If a number of leads are used and any pair of electrodes can be selected a large number of different current paths can be selected. Using the result obtained for the different paths a two- or three-dimensional tomographic image can be calculated based on the results. Furthermore two electrodes can be used to feed current though the tissue and the remaining electrodes can be used to monitor the resulting voltages. This can be used to further enhance the image resolution both in spatial resolution quality and in precision. The information could be presented in numerical form, in graphical form and/or as a calculated tomographic map in two- or three-dimensions. The choice of presentation may depend on the number of current paths used to inform the user about the current state of the tissue and the progress of the ongoing procedure. By using a sufficiently fast computer and appropriate software the information could be presented in real-time, i.e. the collected signals are processed and updated information presented to the operator in a short period of time ranging from less than a second to 20 seconds.

Figure 2:
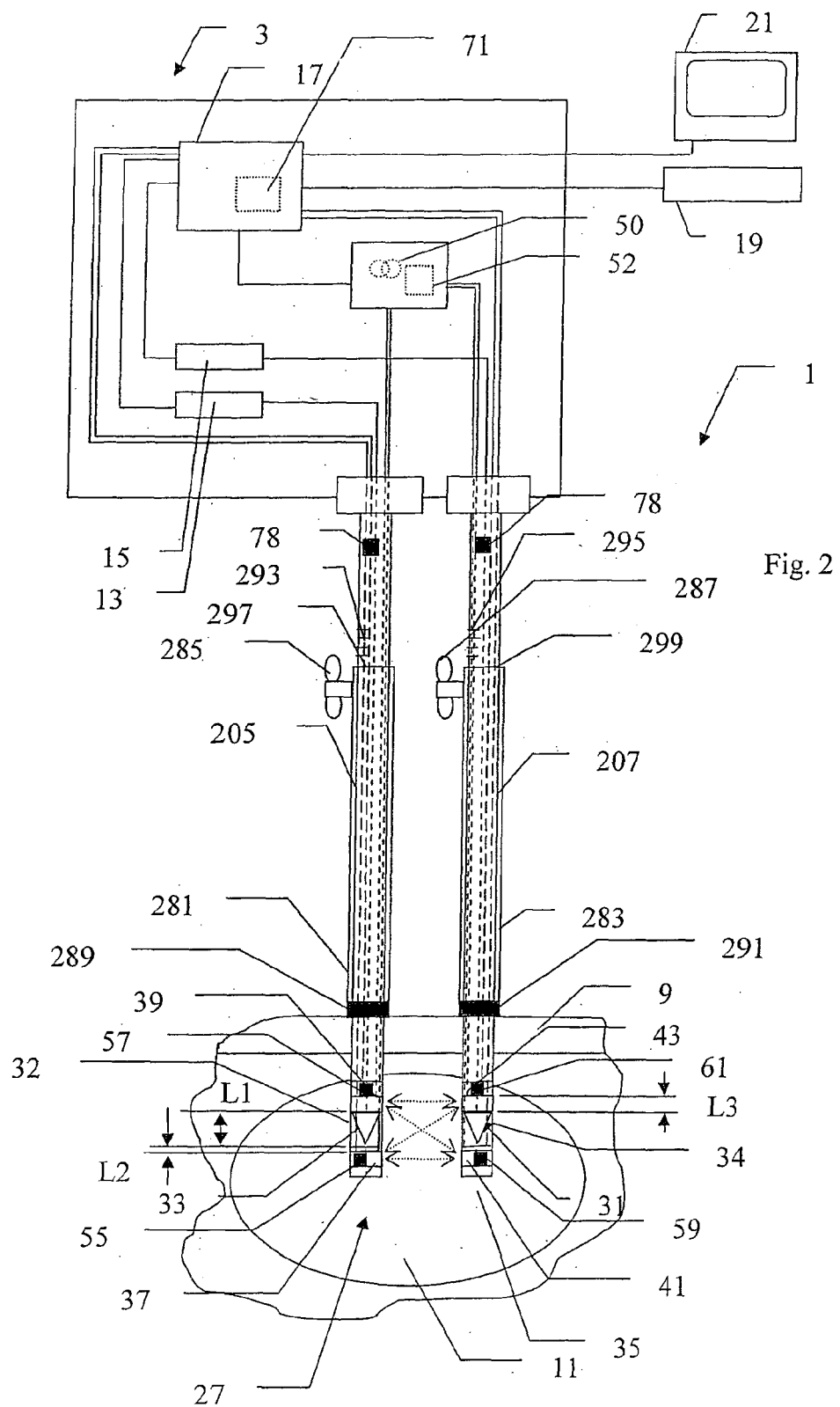
FIG. 2 shows schematically a second embodiment of a thermal device in accordance with the present invention.

A second embodiment of a thermal device in accordance with the present invention is shown schematically in FIG. 2. In this embodiment of a device in accordance with the present invention the depth of each lead inside a patient is determined with the help of movable electrodes. Each lead 205, 207 is provided with a movable sleeve 281, 283 through which the distal end of the respective lead passes. Sleeves 281, 283 are lockable in place on their respective sleeves by a locking means such as a locking screw 285, 287. The distal end of each sleeve 281, 283 is provided with a sleeve-mounted electrode 289, 291 which is intended to be in contact with the patient's skin or the tissue being treated during treatment. Each lead 205, 207 is provided with a graduated scale 293, 295 which can be used to read off the distance that the sleeve-mounted electrode 289, 291 is from the centre of the window of the lead. Before insertion of each lead 205, 207 into the patient, the working depths for the lead is determined, e.g. by scanning to determine the position of the tissue being treated and the appropriate depth for each lead to be positioned at. The appropriate depth can be determined, for example, as the depth that the centre of the window should be from the skin of the patient or, as a second example, as the depth that the centre of the window should be inside an organ, the depth being measured from the surface of the organ.

In a method for using the device in accordance with the second embodiment of the present invention when the depth that the window should be from the skin is known, each lead 205, 207 is passed through a respective sleeve 281, 283 until a reference point of the sleeve, e.g. its upper rim, 297, 299 is adjacent the mark on the scale which corresponds to the desired working depth. The sleeve is then locked at this position. For example if the centre of the window is supposed to be 15 mm below the skin of the patient then the sleeve is locked with its reference point adjacent the 15 mm mark of the scale so that the sleeve-mounted electrode is positioned 15 mm away from the centre of the window. The value of the transfer function of the tissue measured between the sleeve-mounted electrode and a ring electrode e.g. ring electrode 37 on the same lead will be infinity when there is no electrical contact between them. The lead can be inserted into the patient until the sleeve-mounted electrode 289 comes in contact with the skin of the patient at which point the lead 205 is at the desired working depth. This point can be determined from the step change in the transfer function signal which occurs when electrical contact becomes established between the e.g. ring electrode 37 and the sleeve-mounted electrode. Second and subsequent leads can be positioned in the same way. The correct positioning of leads 205, 207 with respect to each other and/or the determination of their actual positions can be achieved by triangulation as described above with reference to the first embodiment of the invention.

In a method for using the device in accordance with the second embodiment of the present invention when the depth that the window should be from the surface of an organ, e.g. the surface of the liver, is known, each lead 205, 207 is passed through a respective sleeve 281, 283 until a reference point of the sleeve, e.g. its upper rim, 297, 299 is adjacent the mark on the scale which corresponds to the desired working depth, i.e. the distance between the surface of the organ and the window. The sleeve is then locked at this position. For example if the centre of the window is supposed to be 20 mm below the surface of the organ of the patient then the sleeve is locked with its reference point adjacent the 20 mm mark of the scale so that the sleeve-mounted electrode is positioned 20 mm away from the centre of the window. The value of the transfer function of the tissue measured between the sleeve-mounted electrode and a ring electrode e.g. ring electrode 37 on the same lead will be infinity when there is no electrical contact between them. The lead can be positioned above the organ and be inserted into the patient. During insertion into the patient the transfer function and/or conductance between distal and intermediate electrodes can be measured in order to determine the conductance and/or transfer function for the tissues and organs that the lead passes through. The values for these tissues and organs can then be compared to the values obtained between the intermediate electrode and the sleeve-mounted electrode to identify the point at which the sleeve-mounted electrode 289 comes in contact with the surface of the organ to be treated—at which point the lead 205 is at the desired working depth. In other words, this point can be determined from the step change in the conductance and/or transfer function signal which occurs when electrical contact becomes established between the intermediate electrode and the sleeve-mounted electrode. Second and subsequent leads can be positioned in the same way. The correct positioning of leads 205, 207 with respect to each other and/or the determination of their actual positions can be achieved by triangulation as described above with reference to the first embodiment of the invention.

In a method for using the device in accordance with the second embodiment of the present invention when the depth that the window should be from the surface of an organ is known, each lead 205, 207 is passed through a respective sleeve 281, 283 until a reference point of the sleeve, e.g. its upper rim, 297, 299 is adjacent the mark on the scale which corresponds to the desired working depth. The sleeve is then locked at this position. For example if the centre of the window is supposed to be 10 mm below the surface of the organ, e.g. the liver, then the sleeve is locked with its reference point adjacent the 10 mm mark of the scale so that the sleeve-mounted electrode is positioned 10 mm away from the centre of the window. The lead can be inserted into the patient and the transfer function between the ring electrodes monitored. When the two ring electrodes enter the healthy tissue of the organ being treated then a steady transfer function value for healthy tissue should be recorded between them until the distal ring electrode enters diseased tissue, e.g. tumour tissue, having a different transfer function, at which point the value of the measured transfer function will change constantly until the intermediate electrode and the distal electrode both are in the same type of diseased tissue. The transfer function of this tissue can be recorded and the value of the transfer function between the sleeve electrode and the intermediate electrode can now be monitored. When the sleeve-mounted electrode 289 comes in contact with the diseased tissue the transfer function value that is being measured between the sleeve-mounted electrode and the intermediate electrode will correspond to that of the diseased tissue and it can be inferred that the sleeve-mounted electrode has just entered the diseased tissue and the window is at the correct working depth. Second and subsequent leads can be positioned in the same way. The correct positioning of leads 205, 207 with respect to each other and/or the determination of their actual positions can be achieved by triangulation as described above with reference to the first embodiment of the invention.

Once leads have been correctly positioned in the diseased tissue, treatment of the tissue can be performed.

Figure 7:
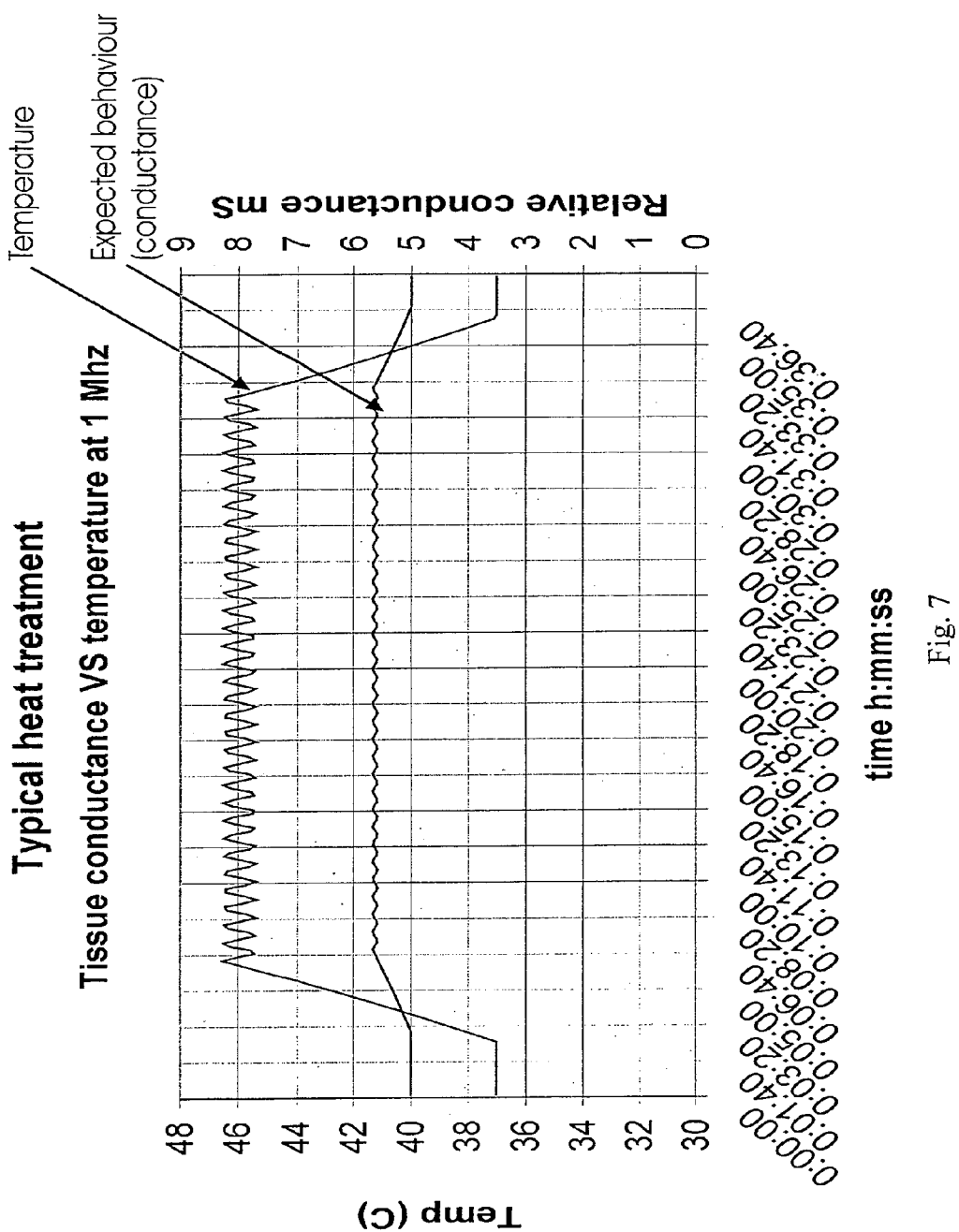
FIGS. 7-11 show graphs showing the effect of temperature on conductivity for different tissue models at two different current frequencies.
Figure 8:
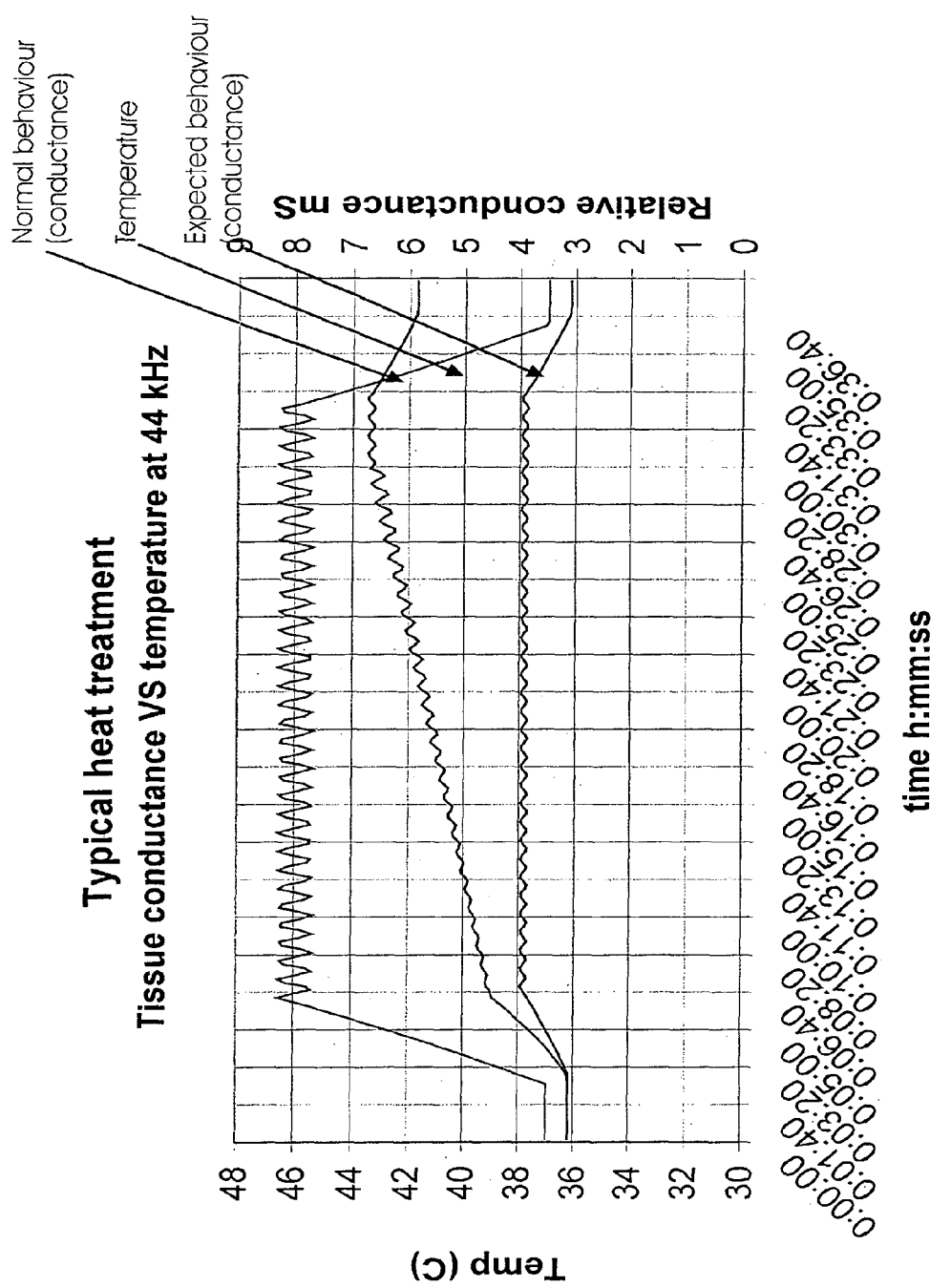

Theoretically, if tissue was only reversibly affected by temperature even when heated to 46° C. the tissue could be heated to 46° C. and temperature responses similar to those shown in FIG. 7 (temperature and conductance versus time when conductance is measured at 44 kHz) and FIG. 8 (temperature and conductance versus time when conductance is measured at 1 MHz) would be obtained. These models show such a theoretical tissue being heated from about 2 minutes to about 32 minutes to a desired temperature of 46° C. with slightly imperfect feedback control so that the actual temperature oscillates above and below the desired temperature. The heating is terminated after 32 minutes, The tissue is allowed to cool and the model shows that the conductance at 37° C. after this prolonged heating is the same as the conductance at 37° C. before heating. An equivalent electrical schematic behaving like tissue according to this theoretical model is very complex as it has a frequency dependency and a thermal coefficient. It thus consists of capacitors, inductors, resistors and thermistors connected in series and in parallel. However when looking at one specific frequency, the frequency dependent components can be removed and a very simplified equivalent circuit can be used.

Thus tissue which is unaffected by heat can be modeled as:

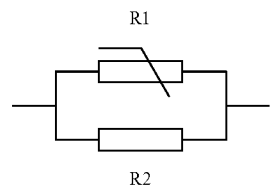

The figure above describes the resistance of a piece of tissue at a certain frequency and in a limited temperature window. It has a starting resistance (mainly R2) and a temperature dependency (variable resistance R1) with a negative temperature coefficient (i.e. comparable to that of a negative temperature coefficient (NTC) thermistor). Thus when the temperature increases the conductivity will go up (i.e. the resulting resistance/impedance goes down).

However in real life tissue, when exposed to heat, above a certain temperature irreversible changes in the properties of the tissue occur. The conductivity will shift in a way that can not be explained in the simplified schematic above. A model for this real-life tissue is as follows:

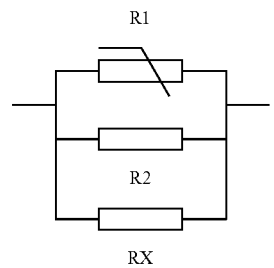

Simplified Equivalent Schematic after Heat
Treatment for Real Life Tissue

In this figure RX has been added. RX is the irreversible influence (the "tissue effect") of a heat treatment at a certain temperature for a certain time.

Normal Conductivity= Starting conductivity+ ($Tcoef *$ temp rise) + integrated (Tissue Effect Constant $*$ (Temp rise $*$ time))

Or ( @44 kHz for tumour EMT6 tissue)

$$3.5 + (0.038 * (T_{act} - 37)) + \int_{t_0}^{t_n} T_{eff} * (T_{act} - 37) * T_{slot}$$

When $T_{slot}$ is a time slot in which a measurement is taken.

Figure 9:
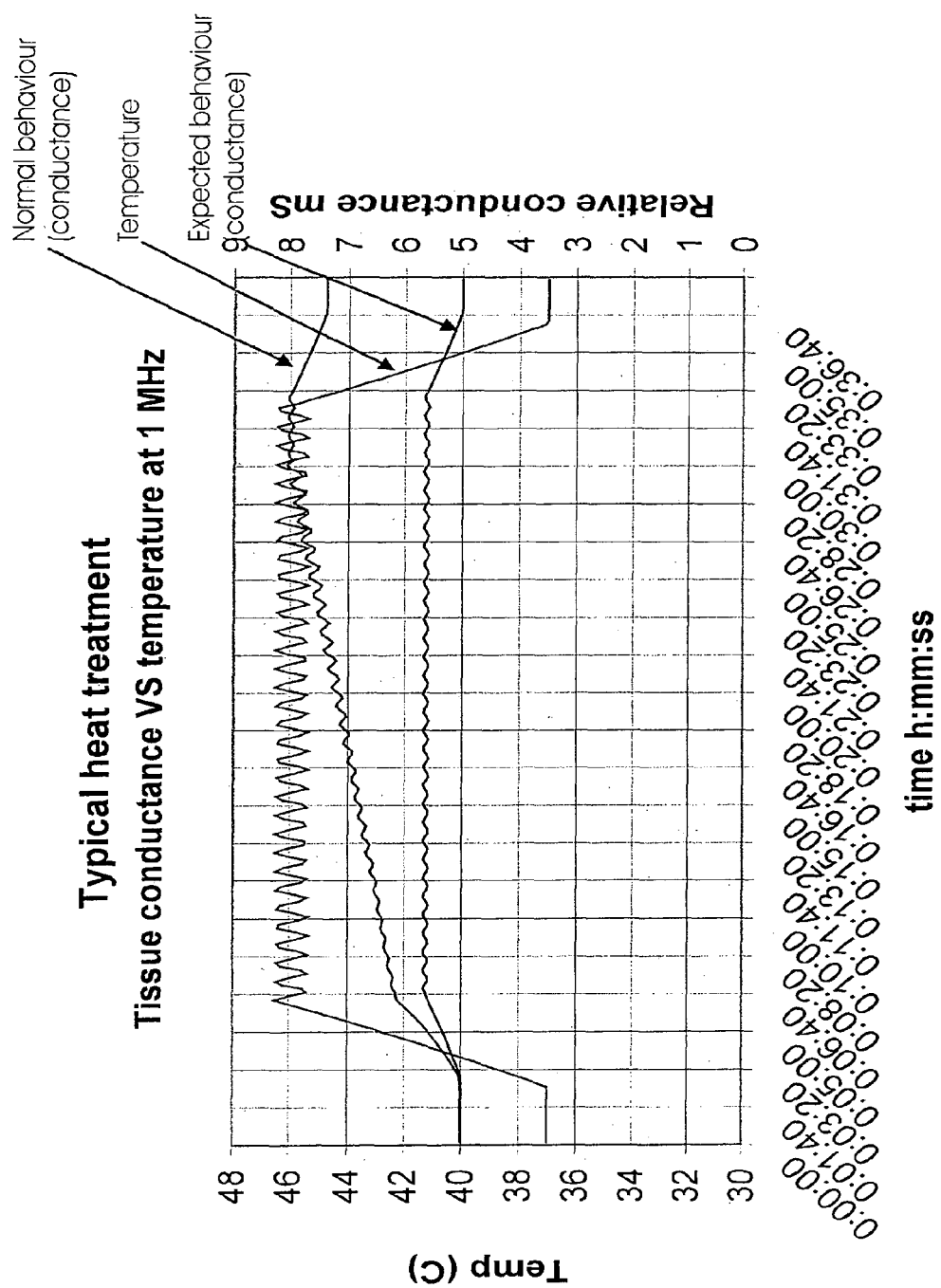
Figure 10:
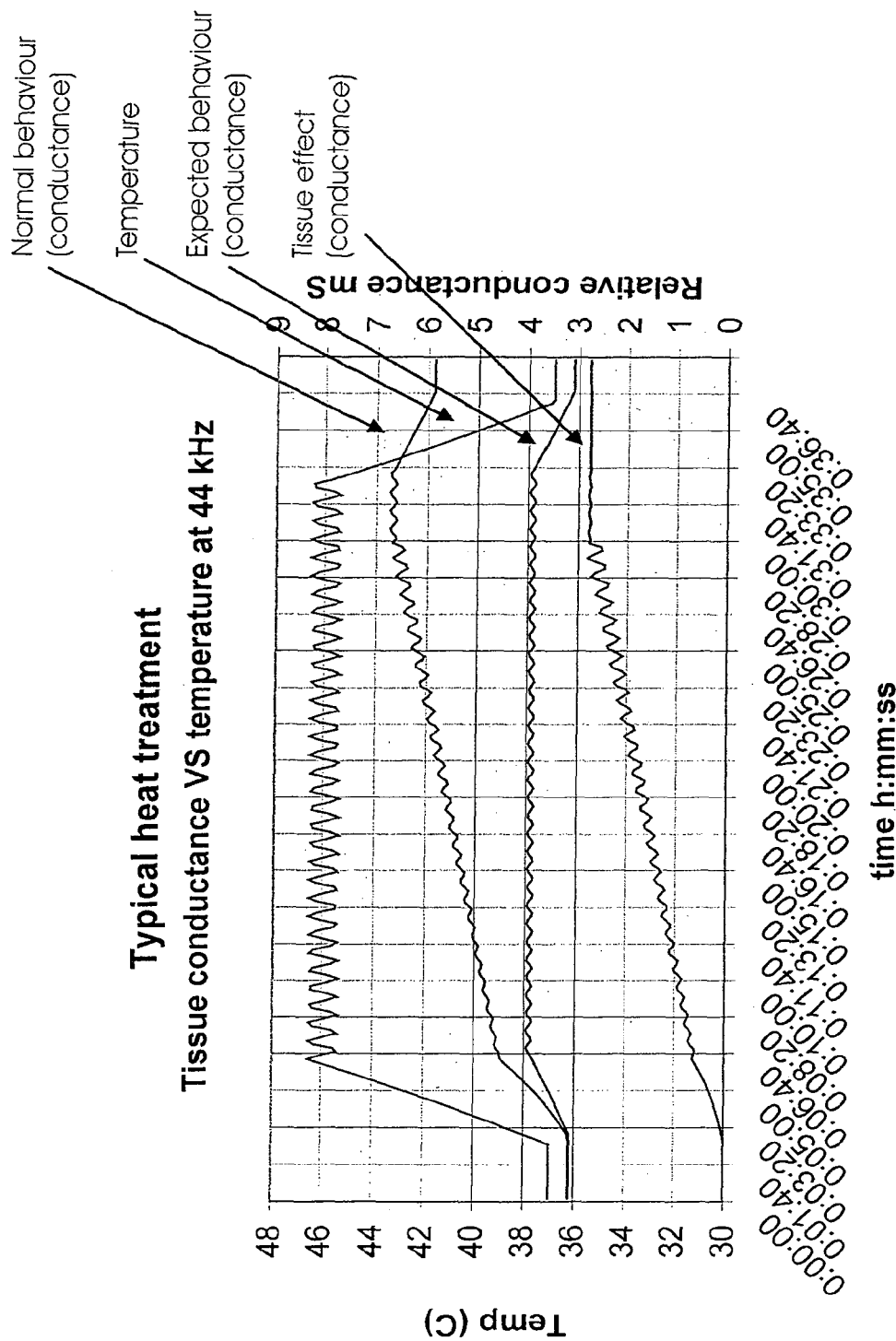
Figure 11:
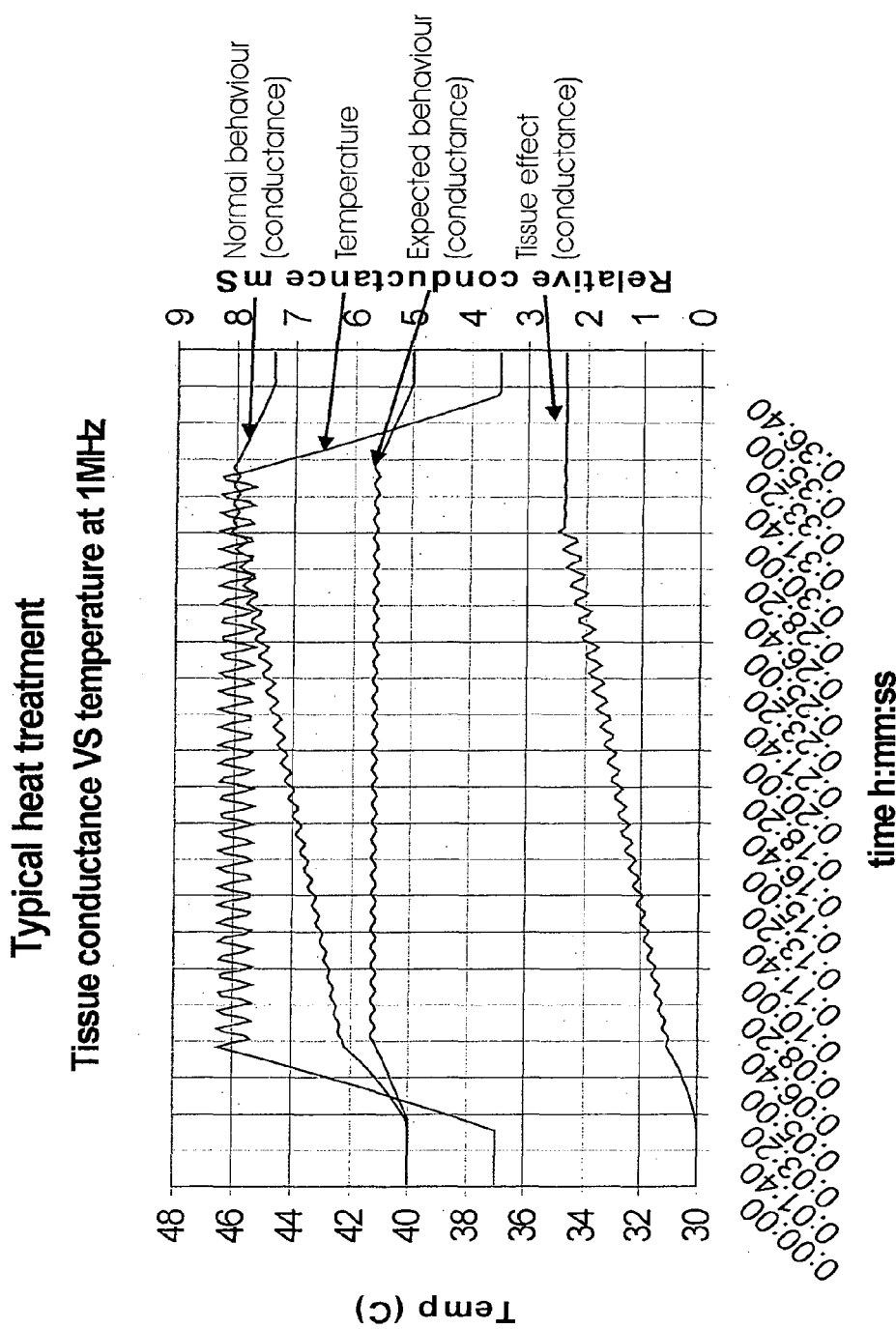

Adapting this model to have the characteristics of EMT6 tumour tissue and plotting temperature and conductance against time, assuming that it takes 30 minutes for all the tissue in the conductance path being measured to be heated at 46° C. and thereby fully irreversibly affected by the elevated temperature, would give curves similar to those shown in FIG. 9 (temperature and conductance versus time when conductance is measured at 44 kHz) and FIG. 10 and FIG. 11 (temperature and conductance versus time when conductance is measured at 1 MHz), where the line "normal behaviour" relates to the real life tissue and "expected behaviour" relates to theoretical tissue of the type shown in FIGS. 7 and 8 which does not suffer irreversible thermal changes. These real life tissue curves show that in real life tissue the conductance rises continuously but at decreasing rates before leveling off. The steepest, first part of the curve up to about 6.5 minutes shows the reversible change in conductance caused by heating. There then follows a less steep, second part of the curve up to 30 minutes which represents increasing numbers of cells in the tissue in the conductance path being measured undergoing irreversible changes i.e. are being killed. The third part of the curve, from 30 minutes until heating is terminated at around 33 minutes, has an average slope which is horizontal, and this indicates that all the cells in the tissue in the conductance path being measured have undergone irreversible changes i.e. are dead. In this part of the curve, continued heating with feedback control will not cause any further changes in the tissue in the conductance path being measured, and the difference in relative conductance between the measured conductance and the expected conductance (that is, the conductance that would be expected if the tissue did not undergo irreversible thermal effects) is at a maximum. At this point further treatment will not have any beneficial effect in the local area as the tissue in that region has already been killed.

A first embodiment of a device in accordance with the present invention for the thermal treatment of tissue comprises software and hardware means e.g. a computer, for running the software for automatically measuring the electrical property of tissue into which leads connected to the device have been positioned.

The software performs the following steps:
activating sources of energy 13, 15 to provide energy to tissue heating elements 32, 34. This causes the tissue in the region near the heating elements to be warmed;
monitoring the temperature sensed by thermal sensors 55, 57, 59, 61 and controlling the heat provided to tissue heating elements 32, 34 so that a predetermined desired temperature is detected and maintained at said thermal sensors 55, 57, 59, 61. Preferably there is a feedback system which prevents large swings in the temperature measured by the thermal sensors;
measuring, storing and processing the value of an electrical property between electrode pairs to determine changes in the measured electrical property, wherein said electrodes are positioned on different leads. This permits the change in the electrical property in the electrical path between the leads to be measured;
deactivating said sources of energy when, after having started changing, said value of an electrical property ceases to change for a predetermined period of time, for example once the property has remained substantially the same for 1 minute or 2 minutes. The electrical property should change continuously as the heat spreads and the region of heated tissue increases and more and more of the tissue in the electrical path in region is killed. Once no further changes in the electrical property can be detected there is no need to prolong the heating as the absence of change indicates that the maximum effect possible by heating in the region between the leads has been achieved, the heating can be terminated and, optionally, a signal made to signify that treatment has been terminated. This signal can alert an operator that the treatment is finished and the leads may be removed from the patient.

In a second embodiment of a method to determine the thermal properties of a tissue in accordance with the present invention, once leads have been correctly positioned in the diseased tissue, the conductance thermal coefficients ($T_{coef}$) of the tissue can be measured. Conductance thermal coefficients are defined by the formula $T_{coef} = \Delta Z_f / \Delta t$, where t is the tissue temperature in degrees C., and $Z_f$ is the conductance measured at frequency f.

Firstly, the reversible conductance thermal coefficient ($rT_{coef}$) of the tissue is determined by applying heat for a short period of time, which is sufficiently short such that the tissue is not heated to temperature where irreversible effects take place in the tissue. Naturally the length of the period of time that the heat can be applied for depends amongst others, on the energy delivered by the heating means, the distance between leads and the thermal properties of the tissue being heated. Preferably this heating phase is controlled and monitored by suitable control, recording and processing software in the control means, arranged so that heating is terminated if the thermal sensors adjacent to the heating means in the tissue register a temperature above a predetermined maximum value, for example 4° C. or 5° C. above the normal tissue temperature This predetermined maximum value is chosen to be sufficiently low that there is no risk of irreversible effects occurring in the tissue. In the following it is assumed that irreversible effects take place above 43° C. and that tissue cells will begin to undergo cell death when exposed to a deadly thermal dose which is greater than a certain value. For example for tumour cells this deadly thermal dose is assumed to correspond to being exposed to a temperature of 46° C. for 30 minutes. Temperatures between 43° C. and 46° C. would therefore require exposure times which are longer than 30 minutes and temperatures above 46° C. would require exposure times of less than 30 minutes to initiate cell death. By using thermal sensors which are positioned adjacent to the heating element, and hence should undergo the highest temperature rise it is possible to ensure that no tissue is heated above the predetermined maximum value. Having the thermal sensors attached to the electrode surfaces used for measuring the electrical property of the tissue ensures that the exact temperature of the electrode surface is known. During this heating phase the temperature and conductance in the near field (i.e. between electrode surfaces and their associated thermistors which are situated on the same lead) are monitored. The heating is switched off and the temperature and conductance allowed to return to the initial value while being monitored. Preferably this is repeated in order to ensure that no irreversible changes take place in the tissue. As the heating is relatively short no permanent tissue effect should be produced. The undamaged (or reversible) conductance thermal coefficient of the tissue can be calculated by software in said control unit based on the changes in conductance and temperature. For example, using the experimental data mentioned above for EMT6 tumour in vivo, the software could determine that the conductivity at 44 kHz and 37° C. is 3.5 mS, with a thermal coefficient of 0.038 mS/° C., and the conductivity at 1 MHz at 37° C. is 5.152 mS with a thermal coefficient of 0.081 mS/° C.

A second step is performed in which heating is intended to produce near field irreversible effects, namely death of the diseased tissue, by controlled heating. The control, recording and processing software causes heat to be applied to the tissue at a preset temperature above 42.5° C. which is preferably below 48° C., further preferably below 47° C. and most preferred at 46° C. The preset temperature is chosen so that it will result in cell death after a period of time but does not cause tumour antigens to coagulate. This preset temperature is selected to avoid instant necrotisation, carbonization, coagulation or ablation of the tissue and thus destruction of the tumour antigens.

During this heating the near field tissue conductance and the temperature are monitored, for example at 10 second intervals. Heating is continued until no further changes in conductivity occur in the near field paths being monitored, i.e. the average gradient of conductance against time is zero. When the conductance gradient is substantially zero, i.e. the value of the conductance has reached a substantially constant value, then the tissue change is permanent and continued heating will not have any further effect on the tissue in the path being measured. The irreversible thermal effect on tissue conductance (the "tissue effect") can then be determined.

When it is time to treat the diseased tissue, the device can be programmed to measure the far field tissue conductance, i.e. the conductance between adjacent leads, both between electrode surfaces at the same depth in the tissue i.e. straight through the tissue, and between electrode surfaces at different depths in the tissue, i.e. diagonally, while the tissue is being heated.

When proportionally the same irreversible tissue effect has measured in all of these far field conductance paths (i.e. the change in conductance which is proportional to the length of each electrical path being measured) then this means that the tissue in all the conductance paths between the leads has been heated to the temperature where cell depth should have occurred. This means that the heat treatment is complete and can be terminated. Preferably this is signaled to an operator by a visual and/or audible signal such as, but not limited to, a screen message, a signal lamp, a bell, a chime or the like.

While the invention has been illustrated by devices and methods in which conductance or a transfer function is measured and the resulting measurements analysed, it is also conceivable to modify devices and methods in accordance with the present invention to use measurements relating to impedance and/or capacitance instead.

While the invention has been illustrated with examples in which a heating element (e.g. a laser light transparent window) on a lead is intended to be positioned at a depth inside a tissue, e.g. a tumour, being treated, it is also conceivable to modify devices and methods in accordance with the present invention so that the heating element is positioned at or near the boundary of the tumour—for example near to but outside the tumour.

While the present invention has been illustrated with examples of methods and devices in which two or more leads are implanted in a patient, it is conceivable in a further embodiment of the present invention that methods and devices may be adapted for use with a single lead.

While the present invention has been illustrated with examples of methods and devices in which a lead comprises two or more electrode surfaces and two or more thermal sensors, it is conceivable in a further embodiment of the present invention to use a lead comprising only one electrode surface and/or only one thermal sensor.

It is conceivable in a further embodiment of the present invention to provide a base unit with a plurality of leads, only one of which is provided with a movable electrode. In this case this lead is preferably positioned first and is then used as a reference lead against which the position of further implanted leads can be determined.

While the invention has been illustrated with lasers as the energy sources, it is possible to use any other suitable source of energy, such as ultrasound transducers, resistive heaters, microwave sources, self-regulating Curie metals, self-regulating positive temperature coefficient resistors, heater elements, hot liquids, etc.

While the invention has been illustrated by examples of embodiments in which thermal sensors are positioned on electrode surfaces, it is also conceivable to position them beside said surfaces or at a short distance from them. However the advantage that the conductance and/or transfer functions measurements can be accurately correlated to the temperature of the tissue surrounding the electrodes will be diminished as the distance between thermal sensors and electrodes increases. Additionally, it is conceivable to use a plurality of longitudinally separated thermal sensors in order to determine the temperature gradient along a lead.

Methods and devices in accordance with the present invention are suitable for use in automated systems for the positioning of implantable leads in a patient and/or for the automated treatment of tissue. In such systems a robot arm or the like is intended to insert the leads and requires information on the actual position of the leads as they are being inserted.

The actual position of the leads relative to each other and/or to a reference point on the placement system and/or the patient during and after insertion can be determined by means of the present invention.

Thermal treatment of the tissue may then take place.

In a conceivable use of the present invention for implanting leads into a patient, the position of at least one lead is monitored by ultrasound or some other imaging system during implantation in order to confirm that the lead is indeed being positioned correctly.

In all embodiments of the present invention, leads can be provided with a hollow tube or other distributing means leading to electrodes and/or thermal sensors to allow the addition of a conductive fluid to said electrodes and/or thermal sensors in order to ensure good electrical and/or thermal connection with the surrounding tissue. Such a distribution means can be used during thermal treatment to add conductive fluid in order to ensure that changes in tissue geometry caused by heating, e.g. tissue shrinkage, do not influence measurements taken using those electrodes and/or thermal sensors.

The above described constructions and methods are for illustrative purposes only and are not intended to limit the scope of the following claims.

The invention claimed is:

1. Device for the thermal treatment of tissue comprising a plurality of implantable electrode surfaces, at least one thermal sensor for measuring temperatures at or near at least one of said electrode surfaces, at least one tissue heating element for heating tissue, a current generator, measuring means for measuring the value of an electrical property between selectable pairs of said electrode surfaces, and a control system for controlling said tissue heating elements, current generator and measuring device, wherein said device comprises memory for storing measured values of said electrical property measured over a period of time and software for processing stored measured values in order to determine a calculated temperature coefficient of the electrical property between at least one selectable pair of electrodes and for determining when the calculated temperature coefficient ceases to change for a period of time.

2. Device in accordance with claim 1 wherein said control means is provided with processing software for recording temperature and for processing measured temperature values and stored measured values of said electrical property in order to calculate the reversible temperature coefficient of said tissue property.

3. Device in accordance with claim 2 wherein said control means is provided with processing software for recording temperature and for processing measured temperature values and stored measured values of said electrical property in order to calculate the irreversible temperature coefficient of said tissue property.

4. Device in accordance with claim 1 wherein said control means is provided with processing software for recording temperature and for processing measured temperature values and stored measured values of said electrical property in order to calculate the irreversible temperature coefficient of said tissue property.

5. Device in accordance with claim 4 wherein it comprises a display means for displaying information relating to said measured electrical property and/or calculated coefficients and/or calculated temperature effects.

6. Device in accordance with claim 5 wherein updated information regarding said measured electrical property is displayed to an operator at least once per second.

7. Device in accordance with claim 4 wherein conductance is measured at a plurality of different current frequencies.

8. Device in accordance with claim 1 wherein it comprises at least one lead having a distal electrode surface, at least one intermediate electrode surface and a tissue heating element positioned between said distal electrode surface and an intermediate electrode surfaces.

9. Device in accordance with claim 8 wherein a lead comprises at least two thermal sensors.

10. Method for measuring the electrical property of tissue comprising the following steps: a) activating sources of energy to provide energy to a tissue heating element on a lead implanted in said tissue wherein said implanted lead comprises at least two thermal sensors for measuring the temperature of the tissue and at least two electrodes for measuring an electrical property of said tissue; b) monitoring the temperature sensed by thermal sensors positioned near said tissue heating element and controlling the heat provided to tissue heating element so that a predetermined desired temperature is detected and maintained at said thermal sensors; c) measuring, storing and processing signals relating to the value of an electrical property between pairs of electrodes; d) deactivating said sources of energy when, after having started changing, said value of an electrical property has ceased to change for a predetermined period of time.

11. Method in accordance with claim 10 comprising the further step of producing a signal that measurement has been terminated.

12. Method in accordance with claim 10 wherein there are at least two leads implanted in said tissue, wherein each said implanted lead comprises at least two thermal sensors and at least two electrodes for measuring an electrical property of said tissue.

13. Method in accordance with claim 10, further comprising software for performing the method.

14. Method for the thermal treatment of tissue comprising the following steps: a) activating a source of energy to provide energy to a tissue heating element on a lead implanted in said tissue, wherein said implanted lead comprises at least two thermal sensors for measuring the temperature of the tissue and at least two electrodes for measuring an electrical property of said tissue; b) monitoring the temperature sensed by thermal sensors positioned near said tissue heating element and controlling the energy provided to said tissue heating element so that a predetermined desired temperature is detected and maintained at said thermal sensors; c) measuring, storing and processing signals relating to the value of an electrical property between a pair of said electrodes for measuring an electrical property of said tissue; d) deactivating said sources of energy when, after having started changing, said value of an electrical property ceases to change for a predetermined period of time.

15. Method in accordance with claim 14 comprising the further step of producing a signal that treatment has been terminated.

16. Method in accordance with claim 14 wherein said electrical property is impedance.

17. Method in accordance with claim 14 wherein there are at least two leads implanted in said tissue, wherein each said implanted lead comprises at least two thermal sensors and at least two electrodes for measuring an electrical property of said tissue.

18. Method in accordance with claim 14, further comprising software for performing the method.

* * * * *